US010625086B2

(12) United States Patent
Choo et al.

(10) Patent No.: US 10,625,086 B2
(45) Date of Patent: Apr. 21, 2020

(54) SYSTEMS, DEVICES, AND METHODS FOR ELECTRIC POWER GENERATION FROM VOCAL FOLDS VIBRATIONS

(71) Applicants: Hyuck Choo, San Marino, CA (US);
Hyun Jun Cho, Pasadena, CA (US)

(72) Inventors: Hyuck Choo, San Marino, CA (US);
Hyun Jun Cho, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 200 days.

(21) Appl. No.: 15/244,980

(22) Filed: Aug. 23, 2016

(65) Prior Publication Data

US 2017/0084815 A1    Mar. 23, 2017

Related U.S. Application Data

(60) Provisional application No. 62/261,160, filed on Nov. 30, 2015, provisional application No. 62/222,397, filed on Sep. 23, 2015.

(51) Int. Cl.
*H01L 41/113* (2006.01)
*A61N 1/378* (2006.01)
(Continued)

(52) U.S. Cl.
CPC ........ *A61N 1/3785* (2013.01); *H01L 41/1136* (2013.01); *H02N 2/188* (2013.01);
(Continued)

(58) Field of Classification Search
CPC ...... H02N 2/181; H02N 2/188; A61N 1/3785; H01L 41/1136
(Continued)

(56) References Cited

U.S. PATENT DOCUMENTS 8,040,022 B2 * 10/2011 Sapir ............... H01L 41/0973
310/311
2005/0226310 A1 * 10/2005 Nakazawa ............. G01K 1/024
374/208
(Continued)

OTHER PUBLICATIONS

Cha, S. N., et al., "Sound-Driven Piezoelectric Nanowire-Based Nanogenerators", Advanced Materials, 2010, vol. 22, pp. 4726-4730.
(Continued)

*Primary Examiner* — Thomas M Dougherty
(74) *Attorney, Agent, or Firm* — One LLP

(57) ABSTRACT

Apparatus and methods are provided for the generation of electrical power from acousto-mechanical vibrations originating from the vocal folds of the human body. The apparatus and methods can include one or more beams comprising a piezoelectric material, such as lead zirconate titanate (PZT), coupled to a power circuitry. Each of the one or more beams can also have a predetermined resonance frequency that is within the dominant frequency range of the human voice. The power circuitry can be adapted to receive the electrical charge received by the one or more piezoelectric beams and to convert the electrical charge into an electric current. The power circuitry can also be coupled to a battery for the storage of the converted energy, which in turn can provide power to implantable medical electronic devices (e.g., neurostimulators or cochlear implants) and/or wearable electronics. Numerous piezoelectric beam shapes, device packaging structures and array configurations are also disclosed that can provide improved power generation and reduced damping effects.

20 Claims, 13 Drawing Sheets

(51) Int. Cl.
  H02N 2/18    (2006.01)
  A61N 1/36    (2006.01)
(52) U.S. Cl.
  CPC ........ *A61N 1/3605* (2013.01); *A61N 1/36007* (2013.01); *A61N 1/36036* (2017.08); *A61N 1/36046* (2013.01)
(58) Field of Classification Search
  USPC ......................................................... 310/339
  See application file for complete search history.

(56) References Cited

U.S. PATENT DOCUMENTS

| | | | | |
|---|---|---|---|---|
| 2006/0217776 | A1* | 9/2006 | White | A61N 1/3785 607/35 |
| 2013/0207520 | A1* | 8/2013 | Near | H01L 41/1134 310/339 |
| 2015/0365018 | A1* | 12/2015 | Inman | H01L 41/1136 607/35 |

OTHER PUBLICATIONS

Chen, S., et al., "On-Demand Power Source for Medical Electronic Implants: Acousto-Mechanical Vibrations from Human Vocal Folds", NAPA Institute 2015 Workshop on Enabling Future Health Care: the Role of Micro and Nano Technologies, Napa, CA, Aug. 24-26, 2015, 2 pgs.

Fakhar, K., et al., "Management of Deep Brain Stimulator Battery Failure: Battery Estimators, Charge Density, and Importance of Clinical Symptoms", PLOS One, 2013, vol. 8, No. 3, pp. 1-8.

Gilja, V., et al., "Challenges and Opportunities for Next-Generation Intracortically Based Neural Prostheses", IEEE Transactions on Biomedical Engineering, 2011, vol. 58, No. 7, pp. 1-18.

He, C., et al., "MEMS Energy Harvester for Wireless Biosensors", Proc. 23rd IEEE Conference in Micro-electro-mechanical Systems (MEMS 2010), Jan. 24-28, 2010, Hong Kong, pp. 172-175.

Kral, A., et al., "Developmental Neuroplasticity After Cochlear Implantation", Trends in Neurosciences, 2012, vol. 35, No. 2, pp. 111-122.

Levy, R., et al., "Intracranial Neurostimulation for Pain Control: A Review", Pain Physician, 2010, vol. 13, pp. 157-165.

Liu, H., et al., "Study of the Wideband Behavior of an In-Plane Electromagnetic MEMS Energy Harvester", IEEE 26th International Conference on Micro Electro Mechanical Systems (MEMS), Taipei, Taiwan, Jan. 20-24, 2013, pp. 829-832.

Mitcheson, P. D., et al., Architectures for Vibration-Driven Micropower Generators, Journal of Microelectromechanical Systems, 2004, vol. 13, No. 3, pp. 429-440.

Roundy. S. J., "Energy Scavenging for Wireless Sensor Nodes with a Focus on Vibration to Electricity Conversion", Ph.D. Thesis, UC Berkeley, 2004, pp. 1-301.

Sandmann, P., et al., "Visual activation of auditory cortex reflects maladaptive plasticity in cochlear implant users", Brain, 2012, vol. 135, pp. 555-568.

Shah, R. S., et al., "Deep Brain Stimulation: Technology at the Cutting Edge", J Clin Neurol, 2010, vol. 6, pp. 167-182.

Stieglitz, T., et al., "Implantable Biomedical Microsystems for Neural Prostheses", IEEE Engineering in Medicine and Biology Magazine, 2005, vol. 24, pp. 58-65.

Szarka, G. D., et al., "Review of Power Conditioning for Kinetic Energy Harvesting Systems", IEEE Transactions on Power Electronics, 2012, vol. 27, No. 2, pp. 803-815.

Tang, W., et al., "Electrostatic-comb Drive of Lateral Polysilicon Resonators", Sensors and Actuators, 1992, A21-A23, pp. 328-331.

\* cited by examiner

SYSTEMS, DEVICES, AND METHODS FOR ELECTRIC POWER GENERATION FROM VOCAL FOLDS VIBRATIONS

CROSS-REFERENCE TO RELATED APPLICATIONS

This application claims priority to U.S. Provisional Application Ser. No. 62/222,397, filed Sep. 23, 2015, and U.S. Provisional Application Ser. No. 62/261,160, filed Nov. 30, 2015, both of which are hereby expressly incorporated by reference in their entirety for all purposes.

FIELD

The subject matter described herein relates to systems, devices, and methods for electric power generation from acousto-mechanical vibrations originating from the vocal folds of a human body, and in particular, for the purpose of powering medical electronic implants and/or wearable electronics.

BACKGROUND

Neurostimulators and cochlear implants are fast growing sectors in the medical industry. For example, neurostimulators have been found to be effective in treating epilepsy, chronic pain, depression, and Parkinson's disease. In addition, implantable neural prostheses also present a great potential in improving the condition of those with physical disabilities. However, many of these medical electronic implants and others (e.g., retinal implants and gastric pacemakers) must use batteries, which require periodic replacement. As a result, batteries are often implanted in the chest area. This may require running long electrical lines through the moving parts of the body, such as the neck, to power the stimulators in the head, for example, or other parts of the body, and cause additional reliability issues.

Using an implantable power generator for medical electronics could provide an effective solution to the aforementioned challenges. However, harvestable energy sources are rare inside the human cranial cavity: there are few photons, and microscale thermal gradients are too small for practical power generation. Similarly, harvesting energy from sound waves has resulted in an insignificant power level because air is a very thin medium and highly ineffective for the propagation of mechanical energy. Ambient mechanical vibrations exist, yet previously studied vibration-driven energy-harvesting approaches suffered from irregular availability and widely varying amplitudes and frequencies of ambient vibrations present in biological environments, which made the resonance-based harvesters inefficient and impractical.

Accordingly, there is a present need for systems, devices, and/or methods for efficiently generating electrical power for use in medical electronic implants and/or wearable electronics.

SUMMARY

Described herein are example embodiments of systems, devices, and methods for electric power generation from acousto-mechanical vibrations originating from the vocal folds of a human body. These embodiments can provide electric power to medical electronic implants, such as neurostimulators, cochlear implants, implantable neural prostheses, retinal implants, gastric pacemakers and other implantable medical electronic devices.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The systems, devices, and methods described herein relate to the generation of electric power from acousto-mechanical vibrations originating from the vocal folds of the human body for the purpose of powering implantable electronic medical devices (e.g., neurostimulators and cochlear implants) and/or wearable electronics. For example, a piezoelectric element, apparatus or device is configured to move in response to the acousto-mechanical vibrations originating from the vocal folds of the human body and thereby generate a voltage or charge. In many embodiments, this piezoelectric element is configured in the form of a piezoelectric beam that oscillates in response to the acousto-mechanical vibrations. For ease of illustration, many of the embodiments described herein will refer to this piezoelectric beam configuration, however other non-beam configurations can be utilized with the embodiments described herein.

In some embodiments, the piezoelectric beams can be configured in an array that can be placed in certain hotspot areas of a patient's head and/or neck. The piezoelectric beams can comprise lead zirconate titanate (or other materials or compounds which have piezoelectric properties), and can be fabricated in a serpentine-shape to align the resonance frequency of the beam with the dominant frequency range of the human voice. The piezoelectric beams can be adapted to receive the acousto-mechanical vibrations and, in response, generate an electrical charge which can then be transmitted to a power circuitry for conversion to an electrical current and stored in a battery as electrochemical energy.

Characterizations of Acousto-Mechanical Vibrations from Human Vocal Folds

Figure 1:
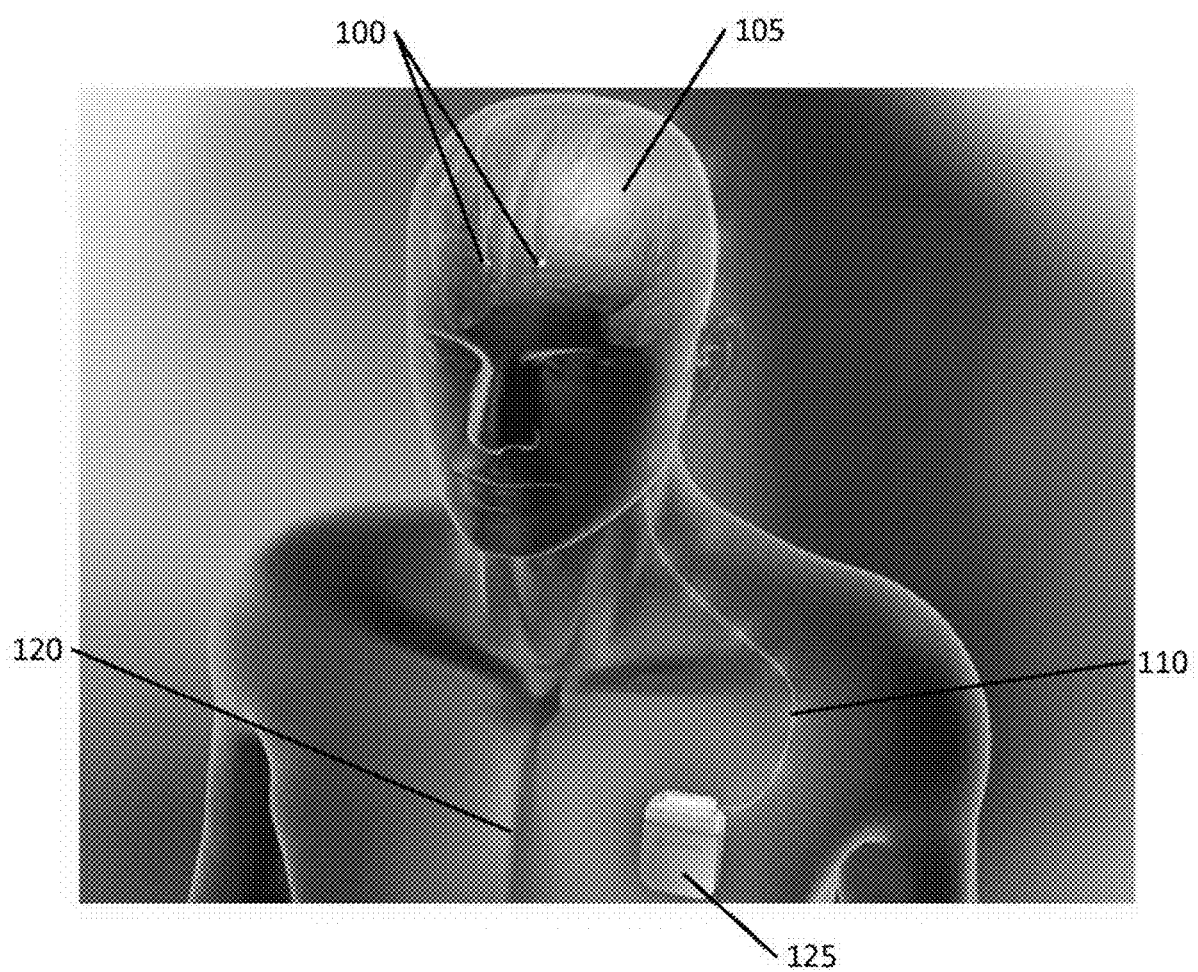
FIG. 1 is an illustration of a neurostimulator coupled to a battery.

Medical electronic implants are a fast growing sector in the medical industry. For example, neurostimulators have been found to be effective in treating epilepsy, chronic pain, depression, and Parkinson's disease. However, these medical electronic implants must use batteries, which require periodic replacement. As a result, batteries are often implanted in the chest area. For example, as shown in FIG. 1, neurostimulators 100 are implanted in a patient's brain 105 and receive electric power from a battery 125 that is implanted in the patient's chest area 120. This may require implanting one or more electrical lines 110 through the moving parts of the body, such as the neck, to power the neurostimulators 100 in the head, and can cause additional reliability issues. Moreover, replacement of the battery 125 may require additional surgery.

To address these challenges, according to certain embodiments of the present disclosure, human vocal folds (also referred to as "vocal cords") can serve as an energy source for medical electronic implants. Vocal folds can serve as an efficient energy source because they function as a built-in tunable function generator, and the air passages and skeletal frames of the human body can effectively serve as "vibration-propagation highways" through the head, neck, and upper torso.

To characterize and measure the acousto-mechanical vibrations originating from the human vocal folds, MEMS accelerometers (e.g., Analog Device's three-axis ADXL327BCPZ and the like) were placed on the skin of male and female participants and secured with non-conducting medical tape. To maintain a consistent vibration amplitude from the vibration source between different measurements, an accelerometer can be kept on the right side of the larynx at the measurement point to serve as a reference point.

Figure 2A:
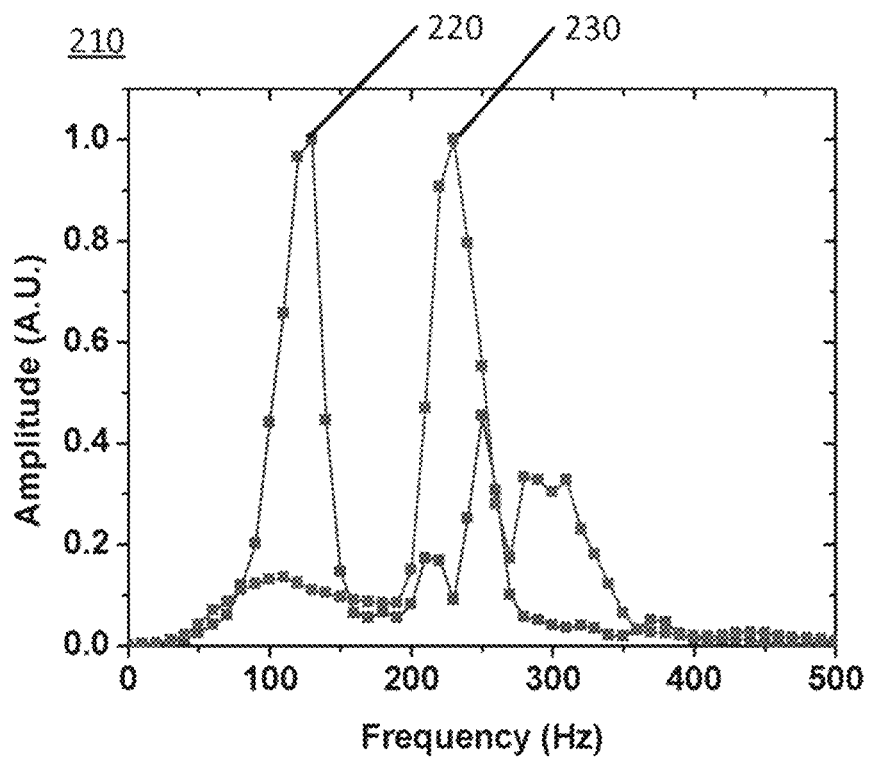
FIGS. 2A and 2B are example graphs illustrating frequency measurements of the human voice.
Figure 2B:
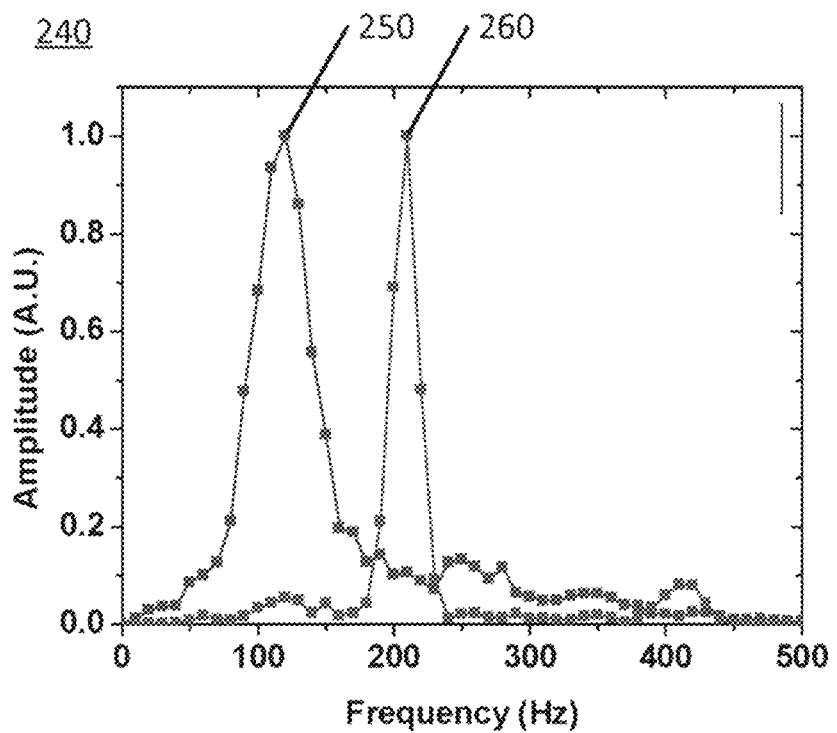

As shown in FIGS. 2A and 2B, dominant vocal vibration frequencies were measured between 90-300 Hz for men and women, with a substantial concentration of the vibration energy residing at the dominant frequencies. For example, FIG. 2A is a graph 210 depicting characterizations of vocal vibrations by amplitude and frequency in male 220 and female 230 participants who were asked to read a paragraph in a natural voice. Similarly, FIG. 2B is a graph 240 depicting characterizations of vocal vibrations by amplitude and frequency in male 250 and female 260 participants who were asked to continuously hum in a scale, from each participant's lowest to highest frequencies. As illustrated in FIGS. 2A and 2B, the acousto-mechanical vibrations from reading 210 and humming 240 show a single dominant peak frequency (between 70 to 90% of the total energy) at approximately 130 Hz and 240 Hz, respectively, for male and female participants.

Figure 3B:
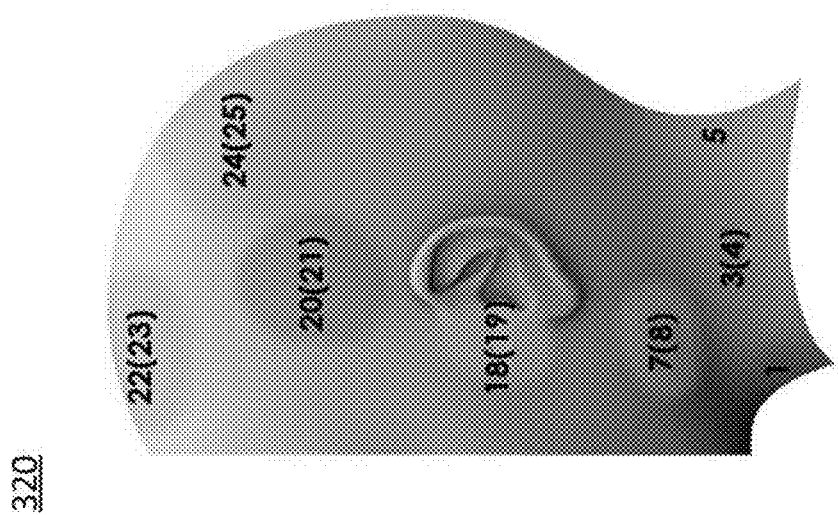
FIGS. 3A and 3B are front and side views, respectively, of an example acousto-mechanical vibration map of the human head.
Figure 3A:
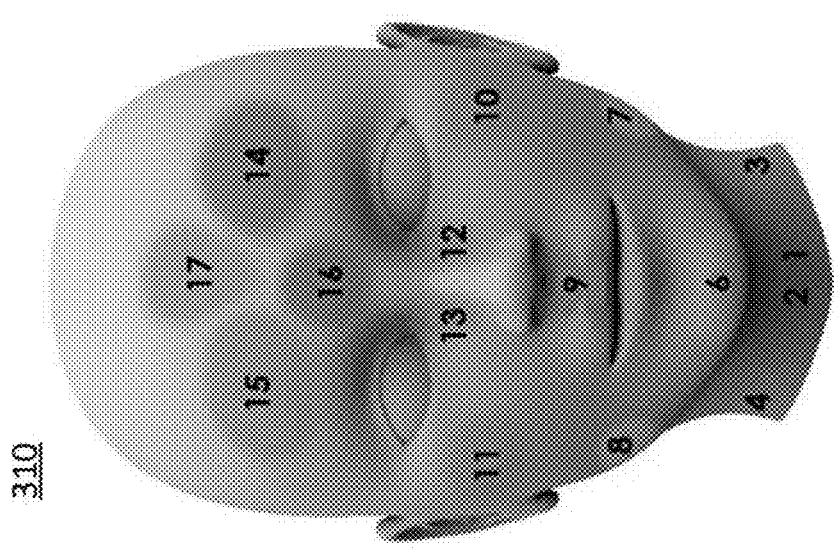

Furthermore, in accordance with the testing procedure described above, the locations of vibration hotspots on the head and neck can be further identified and characterized by measuring the accelerations at multiple locations on the head and neck simultaneously. FIGS. 3A and 3B are front-facing 310 and side 320 views showing acousto-mechanical vibration mapping data from twenty-five (25) different locations in the head. Each enumerated vibration hotspot of the acousto-mechanical vibration map corresponds to a location shown in Table 1 (below).

TABLE 1

Hotspots Corresponding to Acousto-mechanical Vibration Map (FIGS. 3A, 3B)

| | |
|---|---|
| 1 | Larynx L (Ref.) |
| 2 | Larynx R |
| 3 | Neck L |
| 4 | Neck R |
| 5 | Neck - Back |
| 6 | Mandible (Chin) |
| 7 | Mandible (Corner) L |
| 8 | Mandible (Corner) R |
| 9 | Nasal Spine (Lip) |
| 10 | Zygomatic Bone L |
| 11 | Zygomatic Bone R |
| 12 | Nasal Bone L |
| 13 | Nasal Bone R |

TABLE 1-continued

Hotspots Corresponding to Acousto-mechanical
Vibration Map (FIGS. 3A, 3B)

| 14 | Forehead L |
| 15 | Forehead R |
| 16 | Forehead M |
| 17 | Forehead T |
| 18 | Ear L |
| 19 | Ear R |
| 20 | Temporal L |
| 21 | Temporal R |
| 22 | Parietal L |
| 23 | Parietal R |
| 24 | Occipital L |
| 25 | Occipital R |

Referring to FIGS. 3A and 3B, frequency amplitudes generated from constant humming, for example, were high for hotspots along the neck (e.g., hotspots #3 and #4) and nose (e.g., hotspots #12 and #13). Furthermore, the acousto-mechanical vibration map indicates that areas on or adjacent to the larynx (e.g., hotspots #1 and #2) can serve as efficient locations to harvest vocal vibrations. Additionally, the parietal bone (e.g., hotpots #22 and #23) exhibit a possibility of harvesting 50% or more of the energy propagating from the larynx.

Example Embodiments of Piezoelectric Beams

In accordance with several embodiments of the present disclosure, energy from acousto-mechanical vibrations originating from the vocal folds of a human body can be harvested by using one or more piezoelectric beams.

Figure 4A:
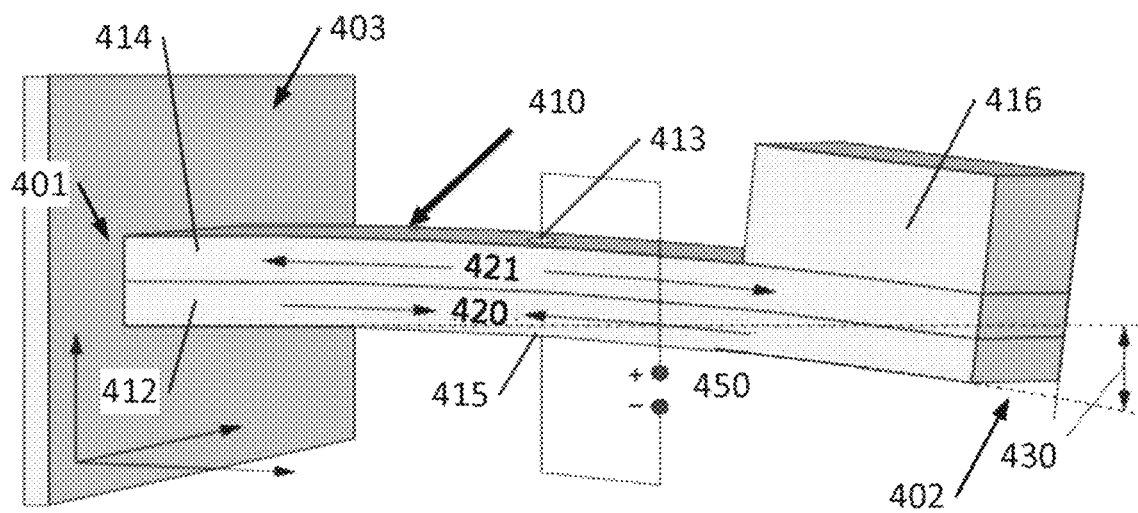
FIG. 4A is a perspective view of an example embodiment of a piezoelectric beam.

FIG. 4A is a diagram showing an exemplary embodiment of a piezoelectric beam 410. In several embodiments, the piezoelectric beam 410 is comprised of lead zirconate titanate (or PZT). Beam 410 can include other materials having piezoelectric characteristics. Specifically, according to the disclosed embodiments, mechanical forces 420 and 421, such as those created by acousto-mechanical vibrations, can be exerted on the beam 410 and can cause the beam 410 to deform (e.g., by vertical displacement) according to a distance or amplitude 430, which in turn, can cause the beam 410 to generate an electrical charge 450.

Here, the beam 410 is in a cantilever-type configuration and has a first end 401 and a second end 402 (each can also be referred to as a terminus). The first end 401 is coupled with (or an integral part of) a base or substrate 403 that can be fixed within a device to remain relatively motionless with respect to the device. The beam 410 has a second end 402 (also can be referred to as a terminus), that is not coupled to the base 403 and is free to move or deflect with respect to the base 403 (or first end 401). In this embodiment, the amplitude 430 is measured as the vertical displacement of end 402 of the beam 410. Generally, a larger amplitude 430 can create a larger strain in the beam 410 which, in turn, can create more voltage and/or power 450.

Beam 410 can include one or more piezoelectric layers and, in the case of multiple layers, each can be formed from the same or a different piezoelectric material. In this embodiment, beam 410 includes one layer that can be modeled as having two regions, a first region 412, a second region 414, and a mass 416. A first electrode 413 is coupled with or present on the first region 412 and a second electrode 415 is coupled with or present on the second region 414. Mass 416 is also coupled with or present on the second region 414. Mass 416 can be the same or a different piezoelectric material, or a non-piezoelectric material. Depending on the needs of the application, mass 416 can be omitted or numerous masses 416 can be included (e.g., such as a second mass on the first region 412 in a position opposite the one shown in FIG. 4A).

Displacement of the beam 410 downwards (as shown here) causes a compressive mechanical force 420 to be applied in first region 412 and causes an expansive mechanical force 421 to be applied in second region 414. These forces act on the piezoelectric material in regions 412 and 414 to generate the charge or voltage 450. Displacement in the opposite direction (upwards) causes an expansive mechanical force to be applied in region 412 and a compressive mechanical force to be applied in region 414, causing the same or a similar voltage 450 to be generated with opposite polarity.

Figure 4B:
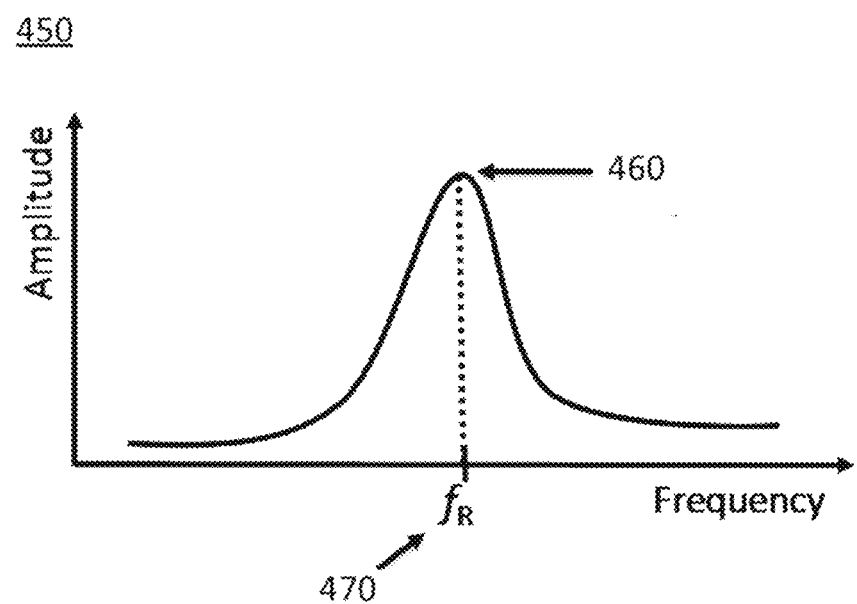
FIG. 4B is a graph showing a frequency of an example embodiment of a piezoelectric beam.

FIG. 4B is a graph 450 showing the frequency and amplitude characteristics of the beam 410 of FIG. 4A. As shown in FIG. 4B, another characteristic of the beam 410 is that it can have a resonance frequency 470 (also known as a "natural frequency"), at which a peak resonance amplitude 460 is achieved. Accordingly, a beam 410 having the depicted frequency curve, can generate an optimal amount of voltage and/or power (i.e., when the peak resonance amplitude 460 is achieved), when it is driven at its resonance frequency 470. The beam 410 can be configured to have an operating frequency range (e.g., the range of frequencies centered around the resonant frequency where significant power is generated). By way of non-limiting example, the operating frequency range can be, e.g., 90 Hz to 300 Hz, which can be a symmetric bandwidth of 210 Hz centered around a resonant frequency of 195 Hz. Any desired bandwidth and resonant frequency can be chosen according to the needs of the application.

The length of the beam 410 from the first end 401 to the second end 402, the height or thickness of beam 410 (and each layer therein), the size of mass 416, and the position of mass 416 along the length of the beam 410, can each be adjusted to change the amplitude response of beam 410 to a particular resonance frequency, and the resonance frequency itself of beam 410.

Figure 5A:
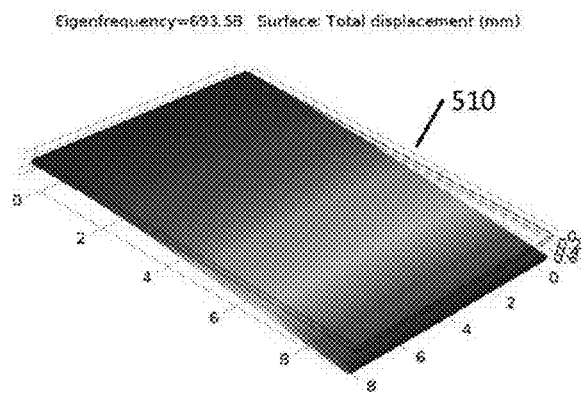
FIGS. 5A and 5B are perspective views of example Finite Element Method (FEM) simulations for measuring displacement in certain embodiments of piezoelectric beams.
Figure 5B:
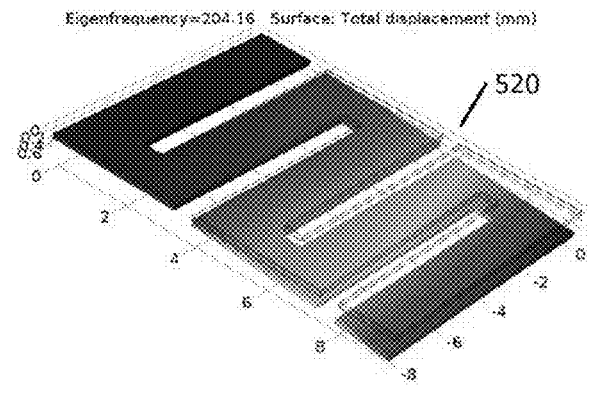
Figure 6A:
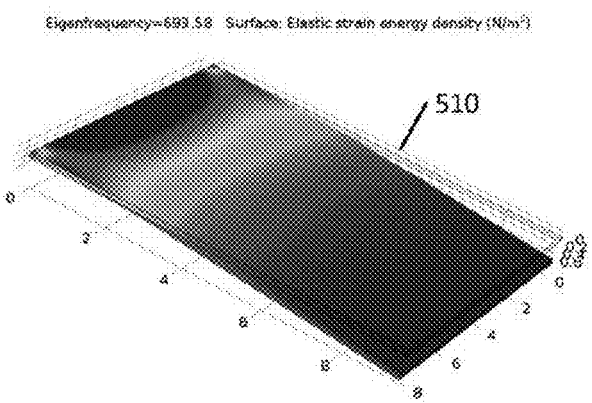
FIGS. 6A and 6B are perspective views of example FEM simulations for measuring elastic strain energy densities in certain embodiments of piezoelectric beams.
Figure 6B:
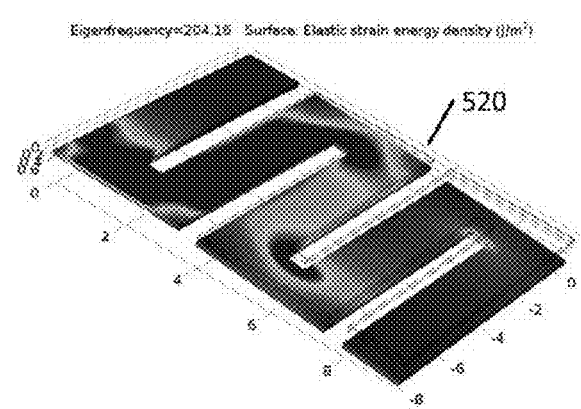

FIGS. 5A, 5B, 6A and 6B show the results of finite element method (FEM) simulations for exemplary embodiments of piezoelectric beams. Specifically, in FIGS. 5A and 6A, a COMSOL simulation of a rectangular PZT beam 510 having a volume of 9.5×8.5×0.127 mm$^3$ is shown. In FIGS. 5B and 6B, a COMSOL simulation of a serpentine-shaped PZT beam 520 is shown also having a volume of 9.5×8.5×0.127 mm$^3$. It will be understood by those of skill in the art that beams of other dimensions (e.g., lengths, widths and thicknesses) and piezoelectric materials can also be implemented.

Turning to FIGS. 5A and 6A, the FEM simulations shown each reflect that the rectangular PZT beam 510, having the aforementioned volume and dimensions, can be characterized as having a resonance frequency of approximately 694 Hz. With respect to FIGS. 5B and 6B, the FEM simulations shown each reflect that the serpentine-shaped PZT beam 520 can be characterized as having a resonance frequency of approximately 204 Hz. Furthermore, the resonant frequencies of fabricated PZT beams can be similarly characterized by testing them systematically with a frequency-tunable vibration generator (3B Scientific U56001). The voltages generated by the beams can be measured, for example, by using a National Instrument X-Series DAQ board with 12.1 kΩ load, and analyzed by using a Lab View program. In accordance with such testing protocols, the resonant frequency (Fr) of a laser-micromachined serpentine PZT beam was measured to be 201 Hz, which closely matched the COMSOL simulation result of 204 Hz. The measured resonant frequency of the rectangular beam was 470 Hz.

Accordingly, in certain embodiments, the serpentine-shaped PZT beam 520, with the aforementioned volume and dimensions, resonates at a frequency within the dominant frequency range of human vocal vibrations (e.g., between 90 and 300 Hz), while its total displacement and elastic strain-energy density remain at levels similar to those of the rectangular beam 510. Each of the embodiments described herein can be configured to have a resonant frequency within the dominant frequency range of human vocal vibrations (e.g., between 90 and 300 Hz). These embodiments can have a wide operating frequency range (e.g., the width of the resonant frequency curve) and can be configured to exhibit a significant amplitude displacement (and thus generate power) across the entire range of frequencies. For example, these embodiments can have an operating frequency range from 90 and 300 Hz. Furthermore, with respect to the resonance bandwidth, these embodiments can have a quality factor (or "Q factor") of approximately 10 or less than 10, and thus can accommodate for high energy generation across a range of frequencies.

Example methods of manufacture for the piezoelectric beams are described herein. For example, rectangular piezoelectric beams (such as beam 510 of FIG. 5A) and serpentine-shaped beams (such as beam 700 of FIG. 7A) can be fabricated from single-crystal, single layer PZT sheets, each having a thickness of 127 µm. PZT beams can be patterned according to a design by using a scriber-breaker (e.g., Dynatex GST-150) for straight edges and/or a laser micromachining tool (e.g., Nd:YAG-UV355) integrated with scanning optics for more complex patterns, such as serpentine shapes. It is to be appreciated that PZT sheets having other (or varying) thicknesses can be used (e.g., less than 200 µm, less than 500 µm, and/or less than 1 mm), to achieve a similar resonance frequency, vertical displacement and elastic strain-energy density, based on, for example, variations in the beam shape and/or pattern.

In some embodiments, for example, a PZT beam can be custom-designed and fabricated to have a resonance frequency that substantially matches the dominant frequency of a specific individual's voice determined after testing that individual. The dimensions of the PZT beam can be altered and then the beam can be cut, etched, patterned, or otherwise fabricated to produce a beam "tuned" to the appropriate frequency, typically in the range from 90 to 300 Hz. For example, for a person having a dominant vocal frequency of 200 Hz, a beam can be produced with a resonant frequency of 200 Hz+/−10 Hz, e.g., a Q factor of approximately 10 or less.

In these and other embodiments the array of beams can each have a different resonant frequency, with the same or different frequency gaps or steps therebetween (e.g., 1, 2, . . . 5, 10, 15 Hz etc.). For example, in one embodiment an array has three beams with 10 Hz steps, such as a first beam with a resonant frequency of 190 Hz+/−5 Hz, a second beam with a resonant frequency of 200 Hz+/−5 Hz, and a third beam with a resonant frequency of 210 Hz+/−10 Hz. Such an array can accommodate for varying dominant frequencies in the voice of individual patients. The patients can also tune their voice, in the form of a hum for example, to match that of the device.

Additional variations from those described herein are fully within the scope of the present disclosure. Likewise, other methods of manufacture for piezoelectric devices are known in the art and can be used to fabricate the various embodiments of piezoelectric beams described herein. As such, it should be understood that the present disclosure is not limited to scriber-breaker and/or laser micromachining tools as methods of manufacture.

Figure 7B:
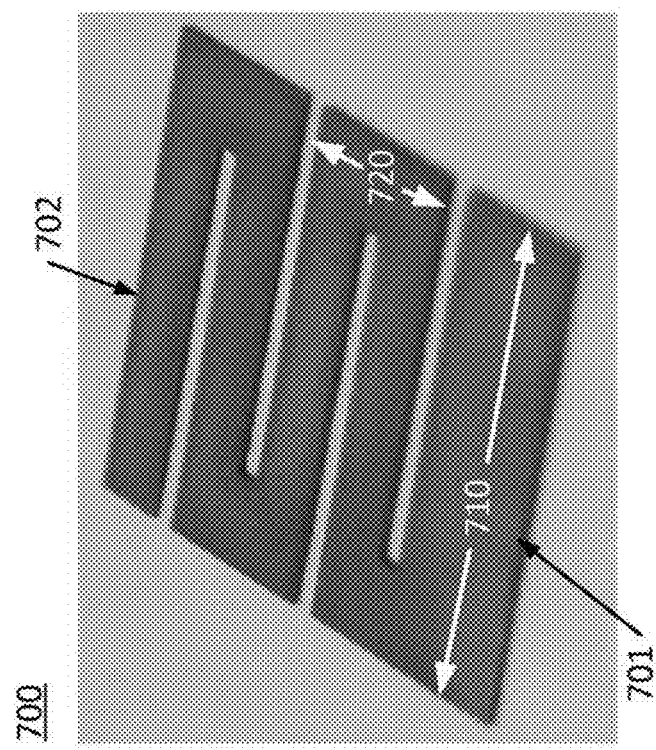
FIG. 7B is a perspective view of one embodiment of a serpentine beam.
Figure 7A:
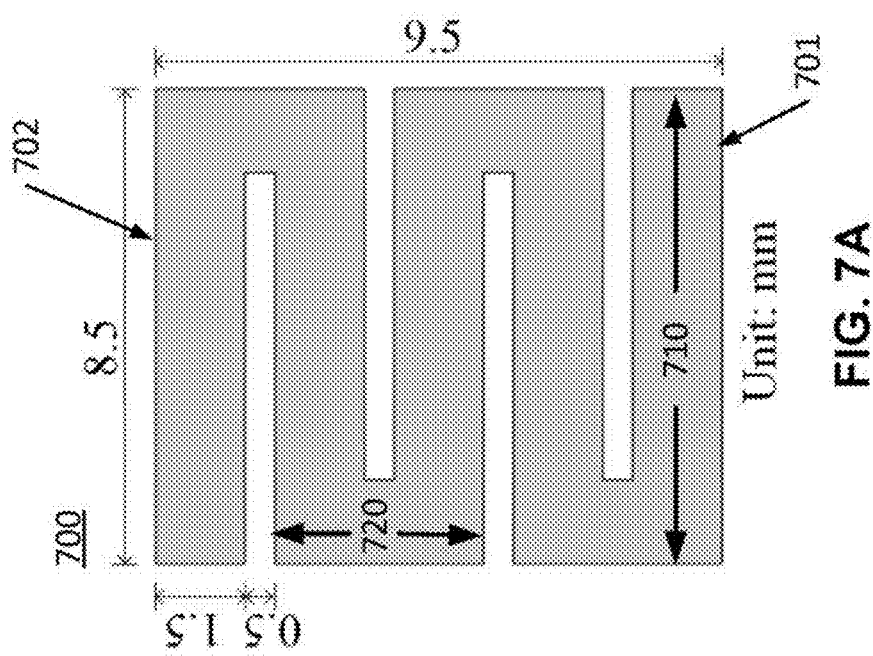
FIG. 7A is a top view of one embodiment of a serpentine beam.

FIGS. 7A and 7B illustrate top-down and perspective views, respectively, of an exemplary embodiment of a piezoelectric beam having a serpentine shape. As with the model used in the simulation, the serpentine-shaped piezoelectric beam can have a volume of 9.5×8.5×0.127 mm$^3$, and can be comprised of PZT, or another material having piezoelectric characteristics.

In some embodiments, as shown in the top-down view 700 of FIG. 7A, a serpentine-shaped beam 700 can be made of a single layer of piezoelectric material. Here, beam 700 can include five lateral segments 710 (extending from left-to-right in the figure) and four longitudinal segments 720 (extending from top-to-bottom in the figure). In this example, each segment 710 has a width of 1.5 mm and a length of 8.5 mm. In these example, gaps exist between adjacent segments 710, each gap having a width of 0.5 mm, although no such gap is required. Here, the outer perimeter of the serpentine-shaped beam 700 forms a rectangular shape, as shown in FIG. 7A, having a width of 8.5 mm and a length of 9.5 mm from first end 701 (which can be coupled to the implantable device) to a second end 702 (which is free to displace). Although described herein by their rectangular segments, the serpentine-shaped beam 700 can be fabricated in a single unitary piece from a single-crystal PZT sheet, as shown in FIG. 7B.

Serpentine-shaped PZT beams 700 of the present disclosure are not limited to the aforementioned dimensions, however, and can be configured to have any number of lengths, widths and thicknesses, such that the beam 700 has a resonant frequency or frequency range that falls within the dominant frequency range of the human voice. For example, beam 700 has five segments 710, although only one segment could be used (similar to FIG. 4A) or any number of two (resulting in a U-shape), three (resulting in an S or Z shape), four, or more segments 710 can be included. The use of multiple segments increases the effective length of beam 700 in terms of its resonant frequency and power generating characteristics without increasing the total length of the device, which would increase its size within the patient's body.

The width of those longitudinal segments 720 oriented at 90 degrees to the lateral segments 710 can be the same as, greater than, or less than the width of each segment 710. For example, in FIG. 7B, the width of segments 720 are the same, each of which is greater than the width of segments 710, which are not the same. The segment 710 closest to the end 701 has a width that is greater than the widths of all of the other segments 710 and 720.

In other embodiments, the serpentine-shaped beam can also have one or more top and bottom electrodes (not shown), wherein the electrodes are comprised of nickel (or a like conductive material). Furthermore, the serpentine-shaped PZT beams can be packaged in a way to minimize unnecessary damping that can occur while passing the vocal fold vibration from the surface of the skin to the PZT beams. For example, in some embodiments, the serpentine shaped PZT beams can be mounted and soldered onto a very solid and light, custom-made mini-PCB board, on which the soldered ends of the PZT beam can serve as anchors.

FIGS. 8A-8C and 9A-9C are graphs further illustrating the frequency, voltage and power characteristics of rectangular and serpentine-shaped PZT beams when excited with 70-dB humming at 100 Hz and 200 Hz respectively. To perform consistent measurements, a sound-level meter (Extech 407730) can be placed three feet away horizontally from the face of a test participant, and the measurements can be taken at the larynx.

Figure 8A:
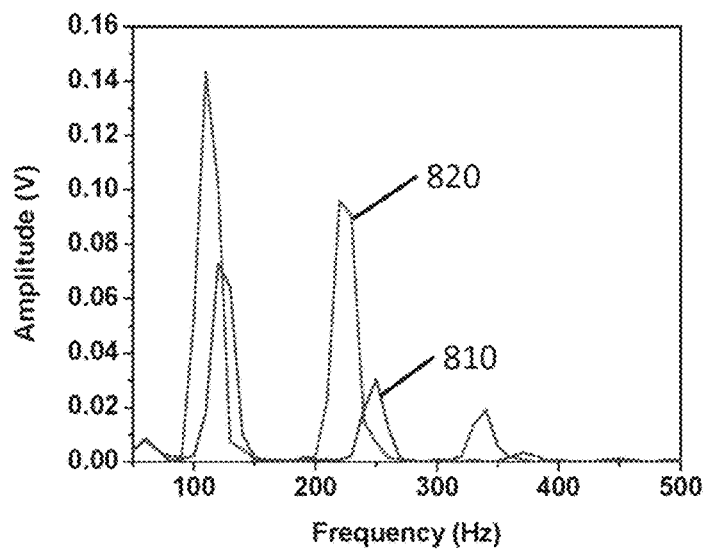
FIGS. 8A, 8B and 8C are example graphs of frequencies, voltages and power generated from example embodiments of a rectangular beam and a serpentine beam.
Figure 8B:
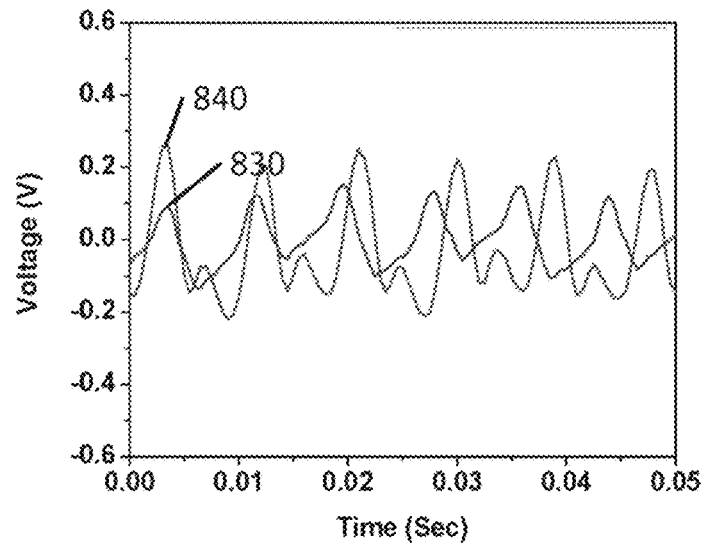
Figure 8C:
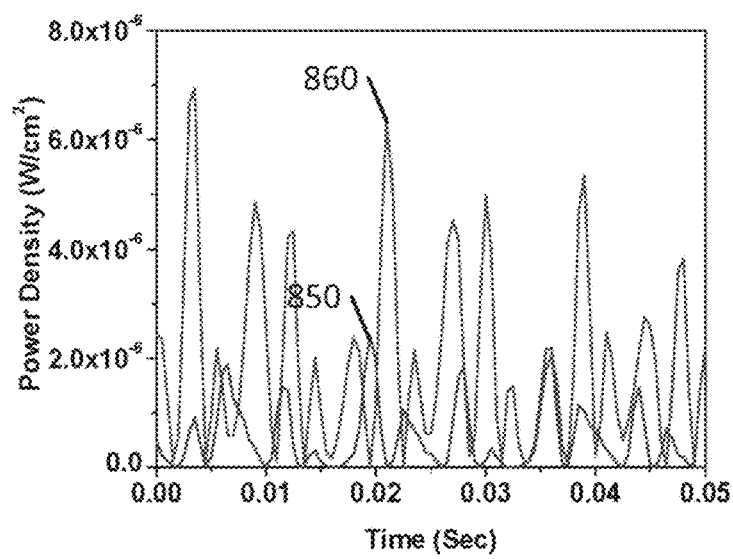
Figure 9A:
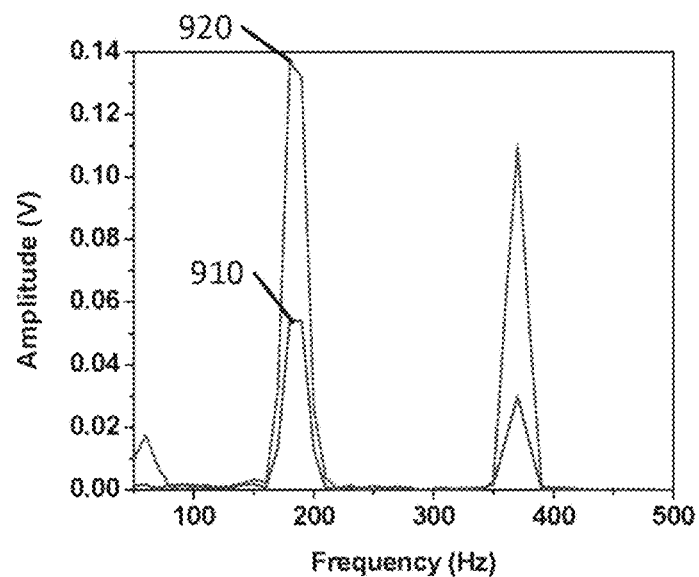
FIGS. 9A, 9B and 9C are also example graphs of frequencies, voltages and power generated from example embodiments of a rectangular beam and a serpentine beam.
Figure 9B:
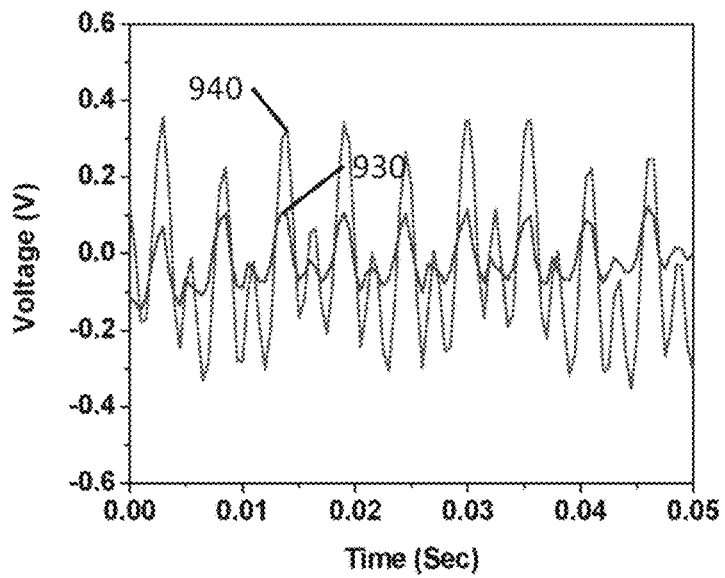
Figure 9C:
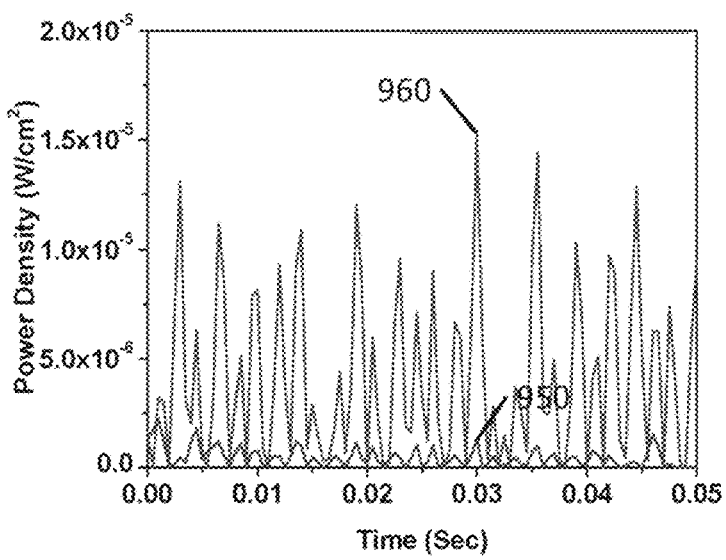

As shown in FIG. 8A, some embodiments, such as the serpentine-shaped PZT beam 820, can exhibit a two-fold increase in voltage swing over other embodiments, such as the rectangular PZT beam 810. Similarly, as shown in FIGS. 9A-9C, the increase in voltage swing 920 and generated power 960 for serpentine-shaped PZT beams relative to rectangular PZT beams 910, 950 can become much larger at 200 Hz because the serpentine-shaped PZT beams may be vibrating at their resonant frequencies.

Furthermore, with respect to power density, in certain embodiments, as reflected at 860 (in FIG. 8C) and 960 (in FIG. 9C), the serpentine-shaped PZT beam can continuously generate 6.9 and 15.3 $\mu W/cm^2$ at 100 Hz and 200 Hz, respectively. In addition, with 100-dB voice (not shown), the serpentine-shaped PZT beam can produce 0.3 $mW/cm^2$. For voice around 120 dB at 200 Hz (not shown), the serpentine-shaped PZT beam can generate an instantaneous peak power at 1.7 $mW/cm^2$.

In certain embodiments, power generation can be further increased by creating an array of energy harvesting PZT beams. For example, in some embodiments, using an area of 5×5 $cm^2$, an array of serpentine-shaped PZT beams can generate continuous power of 7.5 mW or peak power of 42.5 mW, which can be sufficient to power most medical electronic implants.

Example Embodiments of Power Circuitry

Figure 10:
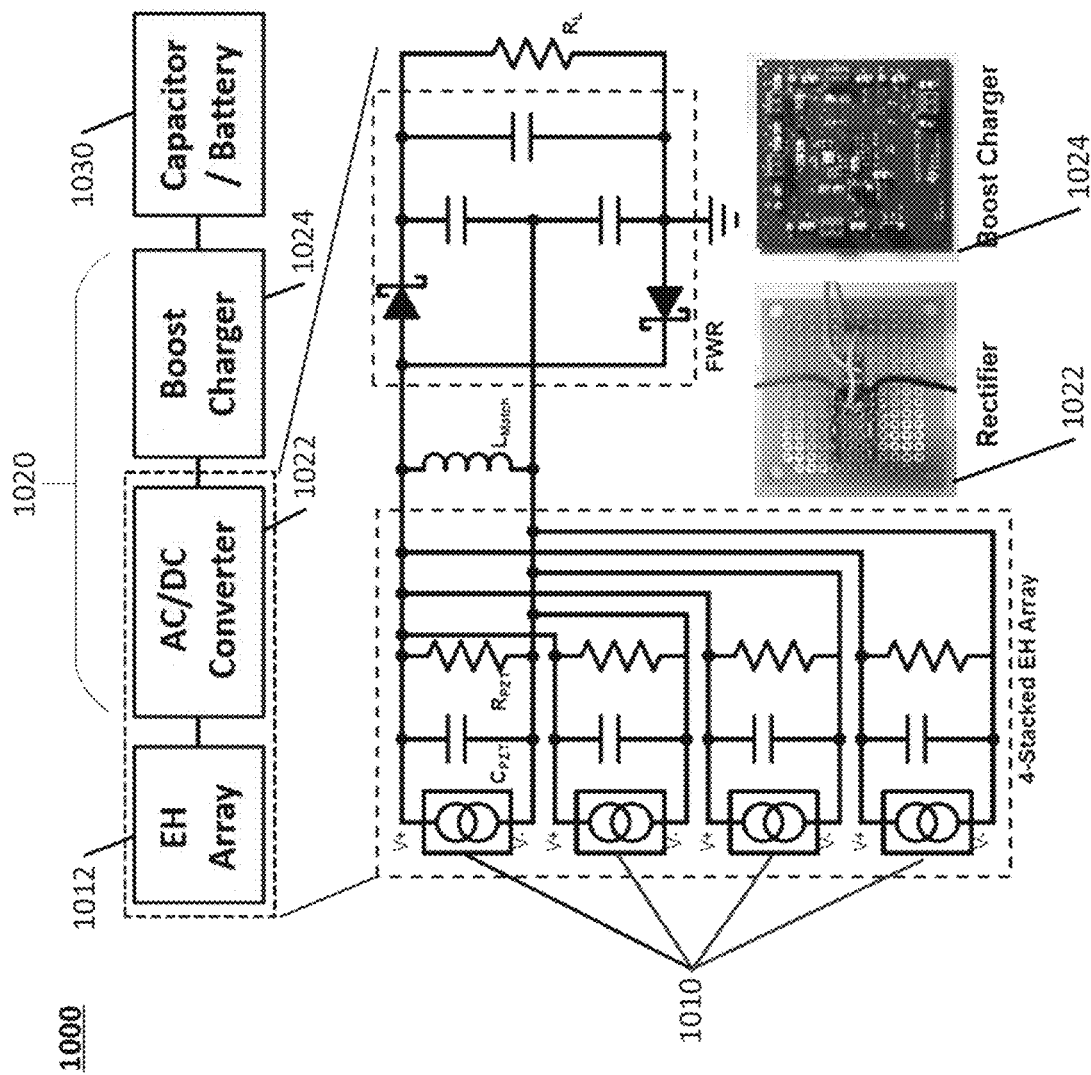
FIG. 10 is a circuit diagram of an example embodiment for electric power generation from acousto-mechanical vibrations.

FIG. 10 is a circuit diagram 1000 of an embodiment for electric power generation from acousto-mechanical vibrations originating from the human vocal folds, utilizing an array of stacked PZT beams. Multiple PZT beams 1010 are schematically depicted in a stacked array 1012. Although the array shown here comprises four PZT beams, it should be understood that, any number of PZT beams 1010 can be configured within the array 1012.

Additionally, in some embodiments, the multiple PZT beams can also be coupled to power circuitry 1020, for example, through one or more electrodes (not shown). Here, each PZT beam 1010 is modeled as a voltage source in parallel with an RC circuit, and the four PZT beams are all connected in parallel. The power circuitry 1020 can be impedance-matched to the array 1012 (e.g., the inductor Lmatch) and can receive the electrical charge generated by the multiple PZT beams 1010, and convert the electrical charge into an electric current. Each PZT beam 1010 generates an alternating current (AC) signal due to the polarity shifting that occurs as the beam oscillates back-and-forth in opposite directions.

For example, in some embodiments, the power circuitry 1020 can include a rectifier 1022 (e.g., an AC/DC converter), which can receive the AC signal from the multiple PZT beams 1010 and convert it into a direct current (DC) signal. Here, the AC/DC converter 1022 is coupled with the array 1010. The power circuitry 1020 can also comprise Schottky barrier diodes, which have a low forward voltage drop and a very fast switching action. In addition, the power circuitry 1020 can also include a boost charger 1024, which can allow for the extraction of more power from the multiple PZT beams 1010. Furthermore, in some embodiments, the power circuitry is coupled to a power storage device 1030, such as a battery and/or capacitor, wherein the battery is adapted to receive the electrical current, convert the electrical current into electrochemical energy, and store the electrochemical energy.

Example Embodiments of Device Packaging and PZT Beam Arrays

Figures 11A, 11B:
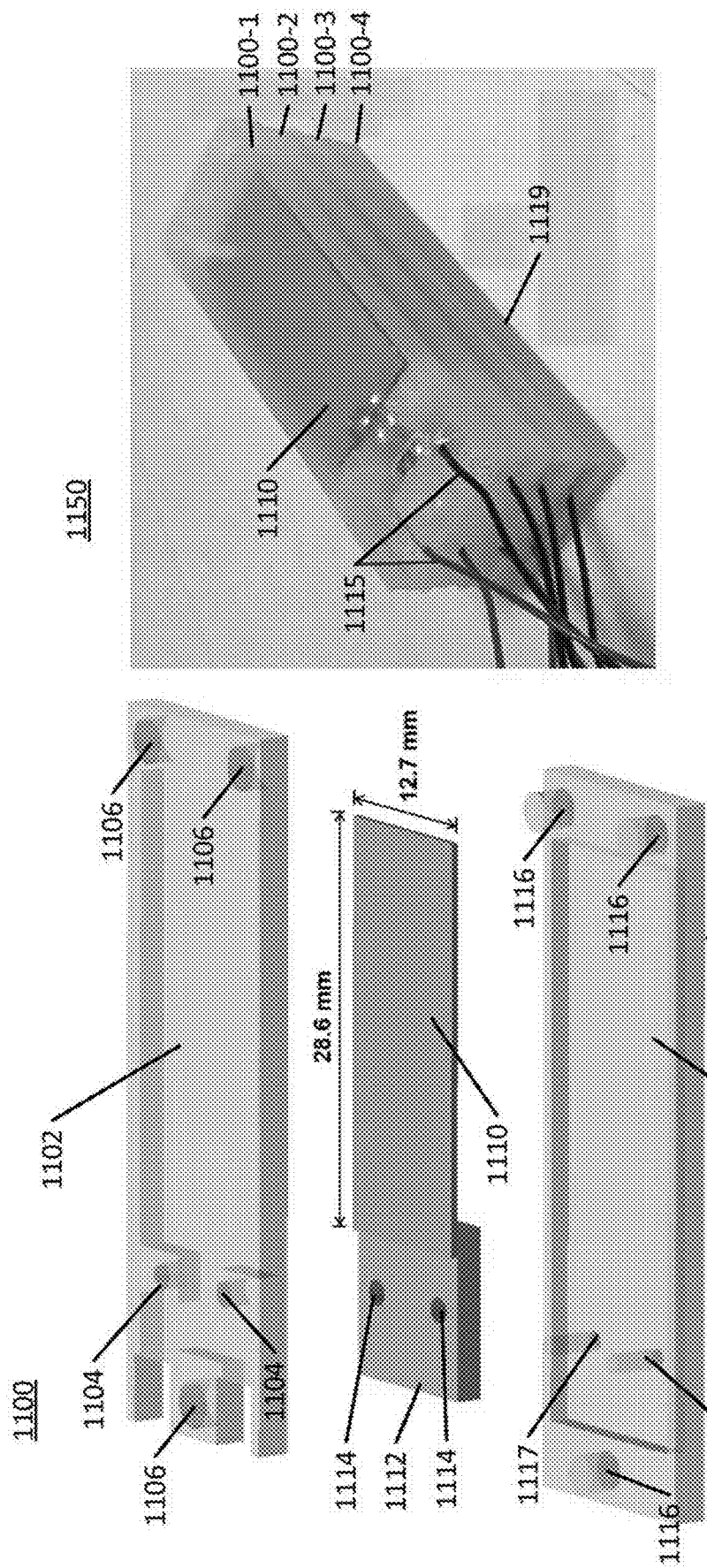
FIG. 11A is a partially exploded view of an example embodiment of a device package for an embodiment of electric power generation from acousto-mechanical vibrations.
FIG. 11B is a perspective view of an example embodiment of an array of devices with one embodiment for electric power generation from acousto-mechanical vibrations.

FIG. 11A is a partially exploded view of a device package 1100 for one embodiment for electric power generation from acousto-mechanical vibrations. FIG. 11A comprises a top structure 1102, a PZT beam 1110 and a bottom structure 1118. Here, the PZT beam 1110 is rectangular, although this package 1100 can be configured for use with any embodiment of the beam described herein. PZT beam 1100 can further comprise an anchoring plate 1112 coupled to a first end of the PZT beam 1100. The anchoring plate 1112 can comprise a conductive material (e.g., nickel) or insulative material, and further include multiple apertures 1114, which can serve as attachment points to the top structure 1102 and the bottom structure 1118.

As shown in FIG. 11A, the anchoring plate 1112 includes two apertures 1114. However, it will be understood by those of skill in the art that the anchoring plate 1112 can be configured to include any number of apertures 1114 (e.g., one, three, four, six, etc.) appropriate for interfacing with the top 1102 and bottom 1118 structures. Additionally, the top 1102 and bottom 1118 structures can include multiple apertures 1104 and 1117, respectively, which align with the multiple apertures 1114 in the PZT beam 1110. In this configuration, multiple posts (not shown) can pass through the aligned apertures 1104, 1114, and 1117, coupling the top structure 1102, PZT beam 1110 and bottom structure 1118, and thereby provide the assembly with structural integrity and reduce any damping effect on the acousto-mechanical vibrations originating from the vocal folds.

According to some embodiments, apertures 1114 in the PZT beam 1110 can further comprise a location for electrodes to couple the PZT beam 1110 with the power circuitry (not shown) described in FIG. 10, and to serve as conduits for the transmission of the electrical charge generated by the PZT beam 1110 to the power circuitry. It will also be understood by those of skill in the art that, instead of the depicted rectangular PZT beam, PZT beams of other shapes and patterns (e.g., serpentine-shaped beam described in earlier embodiments) can be used.

In some embodiments, the top structure 1102 and bottom structure 1118 can further comprise additional apertures 1106 and 1116, respectively. Additional apertures 1106 in the top structure 1102 can be configured to align with the additional apertures 1116 of the bottom structure 1118. Multiple posts (not shown) can pass through the aligned additional apertures, 1106 and 1118, coupling the top structure 1102 and the bottom structure 1118, without directly interfacing with the PZT beam 1110. The additional posts (not shown) can provide the assembly with additional structural integrity and further reduce any damping effect on the acousto-mechanical vibrations originating from the vocal folds. As shown in FIG. 11A, the top structure 1102 and bottom structure 1118 are each configured with three additional apertures 1106, 1116. It will be understood by those of skill in the art, however, that any number of additional apertures can be implemented.

Referring still to FIG. 11A, the bottom structure 1118 further comprises a mounting interface 1119 that can be configured to interface with the patient and receive the acousto-mechanical vibrations originating from the vocal folds. For example, in some embodiments, mounting interface 1119 can be configured to directly adhere to the skin of a patient, for example, through the use of a medical grade adhesive. In alternate embodiments, mounting interface 1119 can be configured for subcutaneous implantation in a patient. In still other embodiments, mounting interface 1119 can be configured for implantation and fixed or secure attachment to a bone surface in the patient, for example, by one or more screws and/or pins.

FIG. 11B is a perspective view of one embodiment of a stacked array of PZT beams 1150, according to the device packaging structures described in FIG. 11A. In some embodiments, for example, the array 1150 can be configured as a single stack of four device packages comprising four PZT beams (i.e., a 1×4 array), as shown in FIG. 11B at 1100-1, 1100-2, 1100-3 and 1100.4. Each PZT beam 1110 is coupled to the power circuitry (not shown) by a pair of wires 1115 coupled to electrodes on the PZT beam. As described earlier, the bottom device package 1100-4 can further include a mounting interface 1119 that can be adapted to attach to a skin layer, subcutaneous layer and/or bone layer of a patient to serve as an interface through which the array 1150 receives acousto-mechanical vibrations originating from the patient's vocal folds.

Figure 12:
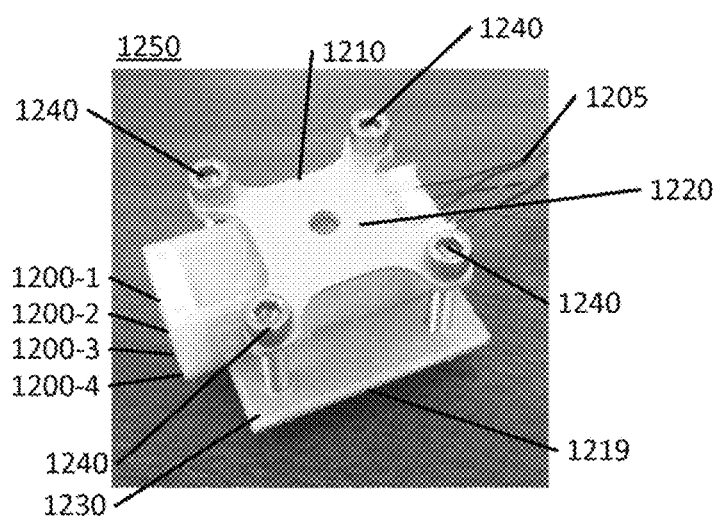
FIG. 12 is a perspective view of an example embodiment of an array of devices with another embodiment for electric power generation from acousto-mechanical vibrations.

FIG. 12 is a perspective view of another embodiment comprising a clamped and stacked array 1250, wherein the array 1250 includes a stack of four device packages (1200-1, 12002, 1200-3 and 1200-4). Each device package comprises a PZT beam which can also include a pair of conductive wires 1205 to couple each PZT beam to a power circuitry, such as the power circuitry described earlier with respect to FIG. 10. In some embodiments, device packages 1200-1, 1200-2, 1200-3 and 1200-4, can be coupled together in a stacked configuration by a clamp 1210 comprising a top clamping portion 1220, a bottom clamping portion 1230, and multiple posts 1240 positioned at each corner of the top 1220 and bottom 1230 clamping portions.

As shown in FIG. 12, the multiple posts 1240 are configured to provide a clamping pressure to the device packages 1200-1, 1200-2, 1200-3 and 1200-4, which are positioned in a stacked configuration between the top 1220 and bottom 1230 clamping portions, wherein each post 1240 can be individually adjustable (e.g., with an Allen wrench) to increase or decrease the pressure between the top 1220 and bottom 1230 clamping portions. In this manner, the clamp 1210 can provide device packages 1200-1, 1200-2, 1200-3 and 1200-4 with structural integrity and can reduce the damping effect on acousto-mechanical vibrations originating from the vocal folds.

In some embodiments, the bottom clamping portion 1230 can further include a mounting interface 1219 that can be adapted to attach to a skin layer, subcutaneous layer and/or bone layer of a patient to serve as an interface through which the clamped and stacked array 1250 receives acousto-mechanical vibrations originating from the patient's vocal folds.

Figure 13A:
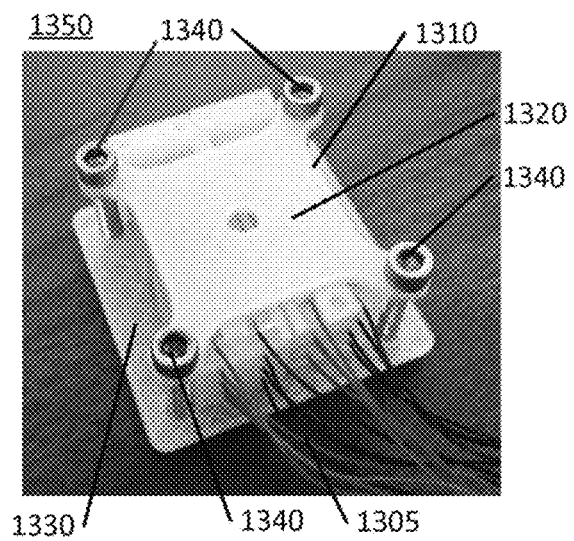
FIG. 13A is a top-down view of an example embodiment of an array of devices with another embodiment for electric power generation from acousto-mechanical vibrations.
Figure 13B:
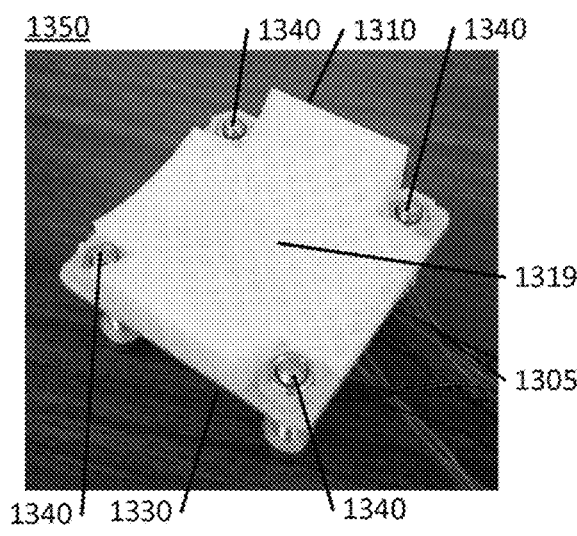
FIG. 13B is a bottom-up view of the example device package shown in FIG. 13A.

FIGS. 13A and 13B provide a top-down and a bottom-up perspective view, respectively, of another embodiment of a clamped and stacked array 1350, wherein the array comprises a 2×4 stack of eight device packages. Each device package comprises a PZT beam which can also include a pair of conductive wires 1305 to couple each PZT beam to a power circuitry, such as the power circuitry described earlier with respect to FIG. 10. As with the embodiment shown in FIG. 12, the device packages can be coupled together in a stacked configuration by a clamp 1310 comprising a top clamping portion 1320, a bottom clamping portion 1330, and multiple adjustable posts 1340 positioned at each corner of the top 1320 and bottom 1330 clamping portions. In this manner, clamp 1310 can provide the device packages with structural integrity and reduce the damping effect on vibrational energy.

Furthermore, as best seen in FIG. 13B, the bottom clamping portion 1330 can further include a mounting interface 1319 that can be adapted to attach to a skin layer, subcutaneous layer and/or bone layer of a patient to serve as an interface through which the array 1350 receives acousto-mechanical vibrations. In some embodiments, the mounting interface 1319 can comprise a flexible, curved and/or textured surface to provide increased friction and stability at the interface between the array 1350 and the patient's body, and further, to enhance transference of vibrational energy to the array 1350.

While FIGS. 12, 13A and 13B each show four posts, wherein each post is positioned at the corners of a square-shaped clamp, it will be understood by those of skill in the art that the clamp can comprise different shapes and sizes (e.g., an oval, circle, or rectangular strip), depending on the application and location for placement of the array, and any number of posts may be used to provide structural integrity and to reduce any damping effect on vibrational energy.

It will also be appreciated by those of skill in the art that in addition to the 1×4 and 2×4 arrays described herein, an array can have any number of device packages depending on the required amount of electrical power. For example, a 10×10 array of 100 device packages can be utilized to produce power close to 16 mW. Furthermore, in some embodiments, for example, an array can be configured as a flexible or curved array to conform to the surface of a patient's skin or bone structure. In some embodiments, for example, the array can include a bottom surface (or "patch") comprising a flexible material, wherein the bottom surface is adapted to adhere to the skin of a patient or, in the alternative, securely attached or fixed to a bone structure (e.g., the parietal bone) of a patient by one or more screws and/or pins. In other embodiments, for example, an array can be configured such that there is a predetermined angle, θ, between one or more adjacent piezoelectric beams, wherein the bottom surfaces of the piezoelectric beams comprise a curved surface. Moreover, although several of the embodiments described herein comprise a lead zirconate titanate (PZT) beam, it will be understood by those of skill in the art that any other piezoelectric materials can be utilized, such as barium titanate, potassium niobate, sodium tungstate, zinc oxide, quartz, berlinite, langasite, gallium orthophosphate, lithium niobate, lithium tantalite, and others. Moreover, those of skill the in art will also understand that piezoelectric materials can be doped using chemicals such as strontium, lanthanum, neodymium, or other similar compounds, depending on the particular application and resonance frequency.

Figure 14B:
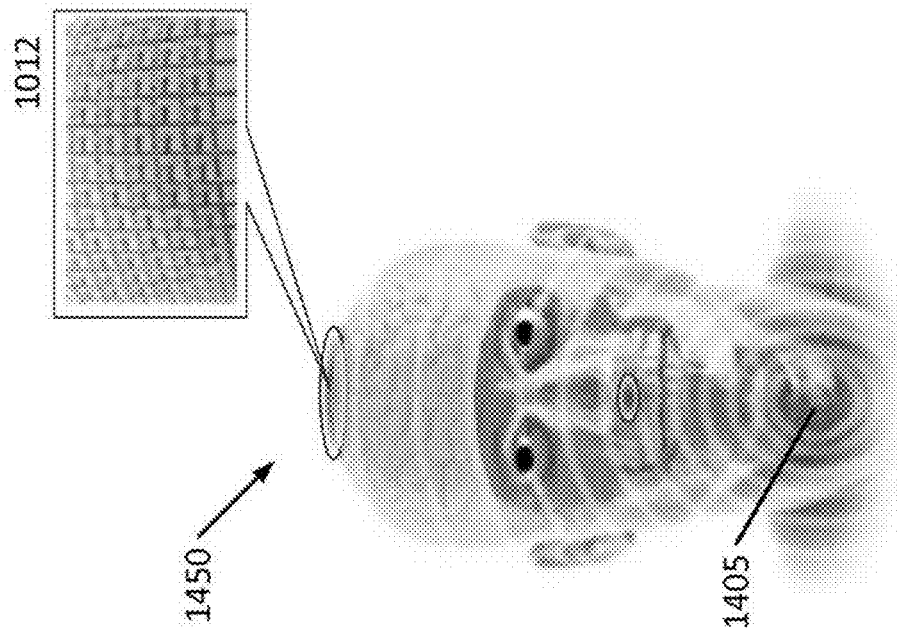
FIG. 14B is a frontal view of a human head coupled with another embodiment for electric power generation from acousto-mechanical vibrations.
Figure 14A:
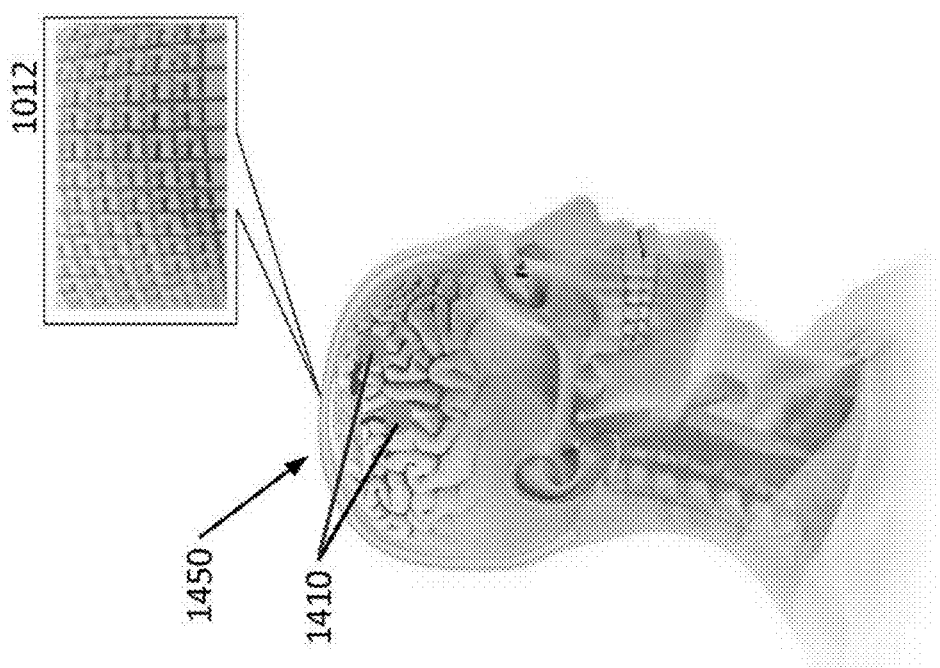
FIG. 14A is a side view of a human head coupled with one embodiment for electric power generation from acousto-mechanical vibrations.
Figure 14C:
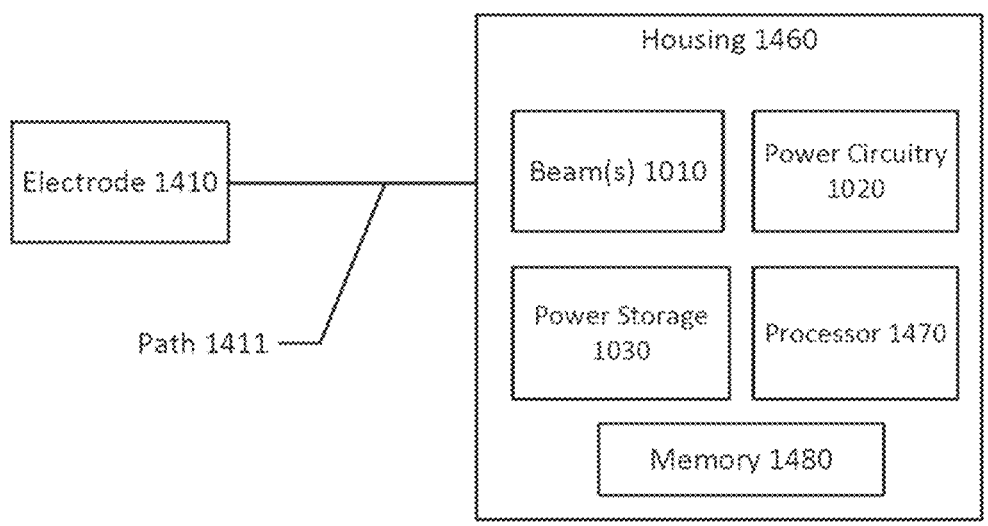
FIG. 14C is a block diagram depicting an example embodiment of a device for electric power generation from acousto-mechanical vibrations.

FIGS. 14A and 14B shows a side view and a frontal view, respectively, of an embodiment of a device 1450 for generating electrical power from acousto-mechanical vibrations for the purposes of powering an implantable electronic medical device. FIG. 14C is a block diagram showing various components of device 1450.

Turning to FIG. 14A, a device 1450 that can include one or more beams (e.g., a single beam or an array), arranged in the manner of FIGS. 11B, 12, 13A and 13B or otherwise, can be implanted in the patient's head such that the mounting interface of the device 1450 is coupled to the patient's body, for example, by adhering to a skin layer, implanting in a subcutaneous layer and/or securing or fixing to a bone surface (e.g., to a surface of the parietal bone) by using one or more screws or pins. The device 1450 can include any number of beams in a stacked or unstacked configuration (e.g., 1×4, 2×4, 10×10), and furthermore, can be coupled together using a clamp, as shown in FIGS. 12, 13A and 13B.

As described in earlier embodiments, each beam (e.g., serpentine-shaped PZT beam) can be adapted to receive acousto-mechanical vibrations 1405 originating from the vocal folds of the patient, as shown in FIG. 14B.

As depicted in FIG. 14C, the device 1450 can include a housing 1460 with the one or more beams 1010 (which can be configured in accordance with any and all embodiments described herein, including as an element other than a beam) and all circuitry contained therein, for example, the power circuitry 1020 and power storage 1030 described with respect to FIG. 10, along with any control circuitry for outputting the power from the power storage 1030. For example, the control circuitry can include one or more processors 1470 and non-transitory memory 1480 storing instructions that, when executed, cause the one or more processors 1470 to cause the application of an electrical stimulus to the tissue of the body adjacent to one or more electrodes or conductive leads 1410, which can be connected to device 1450 by one or more corresponding wires or conductive paths 1411.

The power for this stimulus is derived, at least in part, from the vocal energy harvested by the one or more beams 1010 subsequently stored power storage 1030. The power circuitry 1020 can be configured to receive the AC signal generated by the one or more beams 1010, convert it to DC form, and transfer the DC signal to power storage (e.g., a battery or capacitor) 1030. The storage device 1030 can be configured to provide that power to one or more implantable electronic medical devices or electrode 1410 by way of one or more conductive paths 1411. The storage device 1030 can include separate elements for storing power received from the one or more beams 1010 (e.g., a battery) and for applying some or all of that stored power to the implantable device or electrode (e.g., a capacitor). For example, as shown in FIGS. 14A and 14B, the storage device 1030 can be configured to provide power to multiple neurostimulators 1410 implanted in the brain of the patient. In still other embodiments, the storage device 1030 can provide power to another circuit (e.g., a processor or application specific integrated circuit (ASIC)).

In the embodiment described with respect to FIGS. 14A-C, the beam and circuitry components are located together in the housing 1460, which can be placed at any suitable location in or on the body, such as the top of the head as shown. One or more conductive paths 1411 extend from the housing 1460 to the implanted one or more electrodes 1410. In other embodiments, the conductive paths 1411 can proceed to power another implanted medical device that can have its own circuitry (e.g., a processor and non-transitory memory, etc.). In still other embodiments, the components shown in FIG. 10 can be coupled together in one housing and the harvested power can be supplied to another medical device having its own housing and containing stimulation and control circuitry (e.g., processor 1470 and memory 1480), where that other medical device is placed on or implanted within the patient's body.

In some embodiments, the power circuitry can be integrated into the housing or device packaging of array 1450. In alternate embodiments, the power circuitry can be contained in a separate housing or device package from array 1450, and connected by one or more conductive wires.

Furthermore, although the embodiments herein are described with application to implantable medical electronic devices, it will be understood by those of skill in the art that the systems, methods and devices for electrical power generation from acousto-mechanical vibrations originating from human vocal folds can also be applied to wearable electronics such as, for example, a Bluetooth earpiece, Bluetooth headset, smart watch, smart glasses (e.g., Google Glass), biometric sensor devices and other electronic devices configured to be worn on a human body.

Throughout this disclosure, the preferred embodiment and examples illustrated should be considered as exemplars, rather than as limitations on the present inventive subject matter, which includes many inventions. As used herein, the term "inventive subject matter," "system," "device," "apparatus," "method," "present system," "present device," "present apparatus" or "present method" refers to any and all of the embodiments described herein, and any equivalents.

It should also be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

When an element or feature is referred to as being "on" or "adjacent" to another element or feature, it can be directly on or adjacent the other element or feature or intervening elements or features may also be present. In contrast, when an element is referred to as being "directly on" or extending "directly onto" another element, there are no intervening elements present. Additionally, when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Furthermore, relative terms such as "inner," "outer," "upper," "top," "above," "lower," "bottom," "beneath," "below," and similar terms, may be used herein to describe a relationship of one element to another. Terms such as "higher," "lower," "wider," "narrower," and similar terms, may be used herein to describe angular relationships. It is understood that these terms are intended to encompass different orientations of the elements or system in addition to the orientation depicted in the figures.

Although the terms first, second, third, etc., may be used herein to describe various elements, components, regions, and/or sections, these elements, components, regions, and/or sections should not be limited by these terms. These terms are only used to distinguish one element, component, region, or section from another. Thus, unless expressly stated otherwise, a first element, component, region, or section discussed below could be termed a second element, component, region, or section without departing from the teachings of the inventive subject matter. As used herein, the term "and/or" includes any and all combinations of one or more of the associated list items.

The terminology used herein is for the purpose of describing particular embodiments only and is not intended to be limiting. As used herein, the singular forms "a," "an," and "the" are intended to include the plural forms as well, unless the context clearly indicates otherwise. For example, when the present specification refers to "an" assembly, it is understood that this language encompasses a single assembly or a plurality or array of assemblies. It will be further understood that the terms "comprises," "comprising," "includes," and/or "including" when used herein, specify the presence of stated features, integers, steps, operations, elements, and/or components, but do not preclude the presence or addition of one or more other features, integers, steps, operations, elements, components, and/or groups thereof.

Embodiments are described herein with reference to view illustrations that are schematic illustrations. As such, the actual thickness of elements can be different, and variations from the shapes of the illustrations as a result, for example, of manufacturing techniques and/or tolerances are expected. Thus, the elements illustrated in the figures are schematic in nature and their shapes are not intended to illustrate the precise shape of a region and are not intended to limit the scope of the inventive subject matter.

The foregoing is intended to cover all modifications, equivalents and alternative constructions falling within the spirit and scope of the invention as expressed in the appended claims, wherein no portion of the disclosure is intended, expressly or implicitly, to be dedicated to the public domain if not set forth in the claims. Furthermore, any features, functions, steps, or elements of the embodiments may be recited in or added to the claims, as well as negative limitations that define the inventive scope of the claims by features, functions, steps, or elements that are not within that scope.

What is claimed is:

1. An apparatus for generating electrical power from acousto-mechanical vibrations, the apparatus comprising:
   one or more beams comprising a piezoelectric material, wherein the one or more beams each have a predetermined resonance frequency, and are adapted to receive acousto-mechanical vibrations originating from the vocal folds of a human body, and wherein the one or more beams are further adapted to generate an electrical charge in response to the received acousto-mechanical vibrations;
   a mounting interface configured to secure the apparatus to a skin surface or a bone surface of a patient such that the one or more beams are exterior to or subcutaneously implanted in the patient; and
   a power circuitry coupled to the one or more beams, wherein the power circuitry is adapted to receive the electrical charge generated by the one or more beams, and wherein the power circuitry is further adapted to convert the electrical charge into an electrical current.

2. The apparatus of claim 1, wherein each of the one or more beams at least partially comprises a serpentine pattern.

3. The apparatus of claim 1, wherein the predetermined resonance frequency is between 90 Hz and 300 Hz.

4. The apparatus of claim 1, wherein the one or more beams are configured in one or more stacked arrays.

5. The apparatus of claim 1, wherein the one or more beams are configured in a flexible array.

6. The apparatus of claim 1, further comprising:
   a battery coupled to the power circuitry, wherein the battery is adapted to receive the electrical current, convert the electrical current into electrochemical energy, and store the electrochemical energy.

7. The apparatus of claim 4, wherein the one or more stacked arrays are coupled to the mounting interface by a clamp.

8. The apparatus of claim 1, wherein the mounting interface is further configured for placement on a surface portion of the patient's neck.

9. The apparatus of claim 1, wherein the mounting interface is further configured for implantation on a surface portion of the parietal bone of the human body.

10. The apparatus of claim 6, wherein the battery is further adapted to provide electrical power to a medical electronic implant.

11. The apparatus of claim 10, wherein the medical electronic implant is one of a neurostimulator, a cochlear implant, a neural prosthesis, a retinal implant, or a gastric pacemaker.

12. A method for generating electrical power from acousto-mechanical vibrations, the method comprising:
    securing, by a mounting interface, an apparatus comprising one or more beams to a skin surface or a bone surface of a patient such that the one or more beams are exterior to or subcutaneously implanted in the patient, wherein the one or more beams comprise a piezoelectric material;
    receiving, by the one or more beams, acousto-mechanical vibrations originating from the vocal folds of a human body, wherein each of the one or more beams have a predetermined resonance frequency;
    generating an electrical charge in response to the received acousto-mechanical vibrations;
    transmitting the electrical charge to a power circuitry; and
    converting, by the power circuitry, the electrical charge into an electrical current.

13. The method of claim 12, wherein each of the one or more beams at least partially comprises a serpentine pattern.

14. The method of claim 12, wherein the predetermined resonance frequency of the one or more beams is between 90 Hz and 300 Hz.

15. The method of claim 12, wherein the one or more beams are configured in one or more stacked arrays.

16. The method of claim 12, wherein the one or more beams are configured in a flexible array.

17. The method of claim 12, further comprising:
    receiving, by a battery coupled to the power circuitry, the electrical current;
    converting, by the battery, the electrical current into electrochemical energy; and
    storing the electrochemical energy in the battery.

18. The apparatus of claim 1, wherein the mounting interface comprises a flexible or curved surface disposed between the one or more beams and the portion of the body on which the mounting interface is secured.

19. The apparatus of claim 1, wherein the mounting interface comprises an adhesive adapted to attach the mounting interface to the portion of the body on which the mounting interface is secured.

20. The apparatus of claim 1, wherein the power circuitry includes one or more of a boost charger or Schottky barrier diodes.

* * * * *